United States Patent
Gossling et al.

(10) Patent No.: US 11,337,623 B2
(45) Date of Patent: May 24, 2022

(54) MAPPING THE TRAJECTORY OF A PART OF THE ANATOMY OF THE HUMAN OR ANIMAL BODY

(71) Applicant: 270 Vision Ltd., Hedge End (GB)

(72) Inventors: Martin Gossling, Hedge End (GB); Johannes Vaananen, Hedge End (GB)

(73) Assignee: 270 VISION LTD., Southampton (GB)

( * ) Notice: Subject to any disclaimer, the term of this patent is extended or adjusted under 35 U.S.C. 154(b) by 213 days.

(21) Appl. No.: 16/713,040

(22) Filed: Dec. 13, 2019

(65) Prior Publication Data
US 2020/0113491 A1 Apr. 16, 2020

Related U.S. Application Data

(63) Continuation of application No. 15/511,249, filed as application No. PCT/GB2015/052836 on Sep. 29, 2015, now Pat. No. 10,561,346.

(30) Foreign Application Priority Data

Sep. 30, 2014 (GB) ..................................... 1417282

(51) Int. Cl.
*A61B 5/11* (2006.01)
*A61B 5/00* (2006.01)

(52) U.S. Cl.
CPC .......... *A61B 5/1122* (2013.01); *A61B 5/0015* (2013.01); *A61B 5/7253* (2013.01);
(Continued)

(58) Field of Classification Search
CPC ... A61B 5/1122; A61B 5/0015; A61B 5/7253; A61B 5/743; A61B 2560/0214; A61B 2562/0219
See application file for complete search history.

(56) References Cited

U.S. PATENT DOCUMENTS 5,645,077 A   7/1997 Foxlin
9,173,596 B1  11/2015 Berme et al.
(Continued)

FOREIGN PATENT DOCUMENTS

CA   2698078 A1   9/2011
EP   0 799 597    11/2000
(Continued)

OTHER PUBLICATIONS

English Abstract of JP 2002-000584 A obtained from Lexis-Nexis Total Patent on Mar. 12, 2019, one page.
(Continued)

*Primary Examiner* — Daniel L Cerioni
(74) *Attorney, Agent, or Firm* — Woodard, Emhardt, Henry, Reeves & Wagner, LLP

(57) ABSTRACT

A method for mapping the trajectory of a part of the anatomy of a human or animal body. The method comprises receiving signals from a sensor attached to part of the anatomy, which include three dimensional position information indicating the location of the sensor, determining from the signals at least two angles of rotation of the part of the anatomy to which the sensor is attached with respect to a centre of rotation of another part of the body, transforming the signals to provide two dimensional coordinate data where a first dimension in the two dimensional coordinate space represents a first angle of rotation of the part of the anatomy, and a second dimension in the two dimensional coordinate space represents a second angle of rotation of the part of the anatomy; and stores the two dimensional coordinate data.

20 Claims, 5 Drawing Sheets

(52) U.S. Cl.
CPC ...... *A61B 5/743* (2013.01); *A61B 2560/0214* (2013.01); *A61B 2562/0219* (2013.01)

(56) References Cited

U.S. PATENT DOCUMENTS

| | | | |
|---|---|---|---|
| 9,186,096 | B2 | 11/2015 | Solinsky |
| 9,538,939 | B2 | 1/2017 | Soubeyrat et al. |
| 9,597,015 | B2 | 3/2017 | McNames et al. |
| 2002/0114493 | A1 | 8/2002 | McNitt et al. |
| 2005/0223799 | A1 | 10/2005 | Murphy |
| 2006/0142657 | A1* | 6/2006 | Quaid ................ A61B 17/1703 600/424 |
| 2007/0015611 | A1 | 1/2007 | Noble et al. |
| 2007/0167711 | A1 | 7/2007 | Seki |
| 2009/0322763 | A1 | 12/2009 | Bang et al. |
| 2010/0137706 | A1 | 6/2010 | Viswanathan |
| 2010/0176952 | A1 | 7/2010 | Bajcsy et al. |
| 2010/0261530 | A1* | 10/2010 | Thomas ................ A63F 13/245 463/36 |
| 2011/0218462 | A1 | 9/2011 | Smith |
| 2011/0275957 | A1 | 11/2011 | Bhandari |
| 2012/0130225 | A1* | 5/2012 | Schilling ............. A61B 5/0536 600/411 |
| 2013/0041291 | A1 | 2/2013 | Soubeyrat et al. |
| 2013/0245461 | A1* | 9/2013 | Maier-Hein ........... A61B 5/742 600/476 |
| 2013/0293362 | A1 | 11/2013 | Parazynski |
| 2013/0310711 | A1 | 11/2013 | Wang et al. |
| 2014/0135744 | A1 | 5/2014 | Stein et al. |
| 2014/0136141 | A1 | 5/2014 | Pan et al. |
| 2015/0272484 | A1 | 10/2015 | Ronchi et al. |
| 2015/0320343 | A1 | 11/2015 | Utsunomiya et al. |
| 2016/0310077 | A1* | 10/2016 | Hunter ................ A61B 5/0024 |

FOREIGN PATENT DOCUMENTS

| | | |
|---|---|---|
| EP | 2 199 948 | 6/2010 |
| EP | 2 458 544 | 5/2012 |
| JP | S60-195613 A | 10/1985 |
| JP | 2002-000584 A | 1/2002 |
| JP | 2004-073386 A | 3/2004 |
| JP | 2006-020780 A | 1/2006 |
| JP | 2006-163521 | 6/2006 |
| WO | WO 98/47426 | 10/1998 |
| WO | WO 2011/131497 | 10/2011 |

OTHER PUBLICATIONS

English Abstract of JP 2004-073386 A obtained from Lexis-Nexis Total Patent on Mar. 12, 2019, one page.
English Abstract of JP 2006-163521 A obtained from Lexis-Nexis Total Patent on Mar. 12, 2019, one page.
English Abstract of JP S60-195613 A obtained from Lexis-Nexis Total Patent on Mar. 12, 2019, one page.
Search and Examination Report—dated Sep. 26, 2017.
English translation of JP Office Action dated Mar. 12, 2019 in JP2017-515985.
English Abstract of JP 2002-000584 A.
English Abstract of JP 2004-073386 A machine translation.
English Abstract of JP 2006-020780 A machine translation.
English Abstract of JP S60-195613 A.
EP Search Report dated Sep. 9, 2021 Ser. No. 21174440.4.

* cited by examiner

MAPPING THE TRAJECTORY OF A PART OF THE ANATOMY OF THE HUMAN OR ANIMAL BODY

CROSS-REFERENCE TO RELATED APPLICATIONS

This application is a continuation of U.S. patent application Ser. No. 15/511,249 filed Mar. 15, 2017, which is national stage of PCT/GB2015/052836 filed Sep. 29, 2015, which claims the benefit of GB 1417282.9 filed Sep. 30, 2014, all of which are hereby incorporated by reference.

FIELD OF THE INVENTION

The present disclosure relates to a method and apparatus for mapping the trajectory of a part of the anatomy of the human or animal body.

BACKGROUND

Understanding the trajectory or range of motion of a part of the anatomy can be very useful, both for sportspersons in training and recovering from injury, but also the elderly or those recovering from surgery including animals such as horses and dogs. Typically all of the low cost available measures of trajectory or range of motion are subjective and difficult to repeat or verify. However, veterinary surgeons, orthopaedic surgeons, sports scientists, physiotherapists, care homes and general practitioners (GPs) would all greatly benefit from an objective measurement of some kind. Insurance companies and other professional organisations are also looking for 'Evidence Based Outcomes' where physical data is now required to prove the effectiveness of any treatment or surgery.

Methods currently being used in the art are very basic, often comprising a goniometer, a ruler or simply by done by sight. This makes the data currently available very crude and of poor accuracy and difficult to store and recall. In addition, the data is limited to motion in one dimension/direction, for example the data is limited to a measurement of the range of motion of a limb in flexion and extension. This makes the data difficult to understand usefully, as the range of motion of a limb, for example, may vary depending on the degree of motion in another dimension/direction. There is therefore a requirement for simple, cost effective analysis of complex goniometry.

With the increasing use of health insurance to cover physiotherapy and the number of sporting injuries rising, it is clear that better methods need to be found to assess the status of a patient, especially with the requirement for evidenced based outcomes.

SUMMARY OF THE INVENTION

Aspects of the invention are as set out in the claims.

DRAWINGS

Embodiments of the disclosure will now be described, by way of example only, with reference to the accompanying drawings, in which.

SPECIFIC DESCRIPTION

Figure 1:
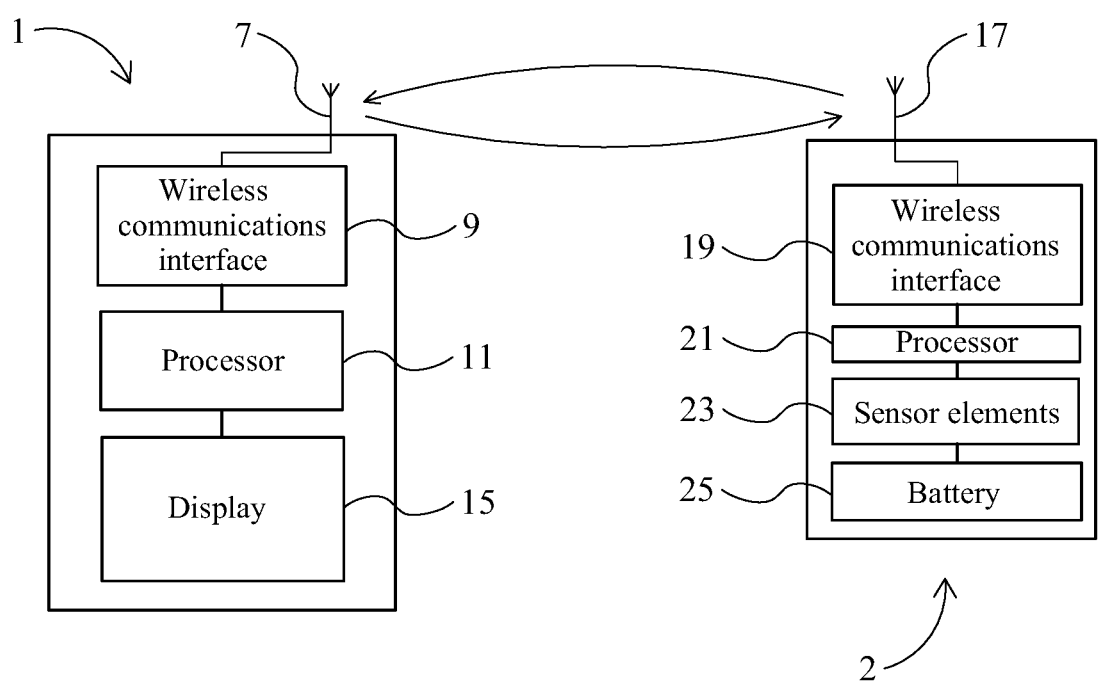
FIG. 1 shows a schematic view of an example apparatus for mapping the trajectory of a part of the anatomy of the human or animal body.

Methods and apparatus for mapping the trajectory of a part of the anatomy of the human or animal body, for example a limb such as an arm or a leg, are described herein. For example the methods and apparatus may allow the range of motion of a part of the anatomy to be determined.

One method comprises attaching a sensor, for example a wireless sensor, to a part of the anatomy, and receiving signals from the sensor comprising three dimensional position information indicating the location of the sensor. From the signals, at least two angles of rotation of the part of the anatomy are determined, for example any two of pitch, yaw and roll.

The signals are transformed to provide two dimensional coordinate data in a two dimensional coordinate space. In the two dimensional coordinate space, one dimension represents a first angle of rotation, and a second dimension represents a second angle of rotation. The signals may be mapped to an image space for displaying the trajectory of the part of the anatomy, for example on a two dimensional plot. For example, the two dimensional coordinate data may be mapped to an image space for display of the trajectory of the part of the anatomy.

Advantageously this allows the results to be displayed on a unique, live, animated display which is an easy to understand graphical representation of the patient moving, which may show, for example, current and maximum displacement of at least two angles of rotation of the part of the anatomy, for example pitch and yaw. In this way the trajectory and/or range of motion of a part of the anatomy may be mapped and tested.

A third angle of rotation of the part of the anatomy, for example roll, may be obtained and stored as an association with the two dimensional coordinate data. The third angle of rotation may be mapped to display locations in an image space, for example the same image space, and overlaid on the display of the trajectory of the part of the anatomy.

Data can be compared to previous mappings, for example stored data can be mapped to an image space, for example the same image space, and overlaid on the display of the trajectory of the part of the anatomy, so that a clinician/physiotherapist and the patient can immediately see the impact of therapy. Not only does this provide encouragement to the patient to continue with their rehabilitation, it also provides Health Insurers with tangible proof of the positive outcome of the treatment.

The patient's maximum ranges for passive and active movement may be indicated on the display, for example by mapping these ranges to display locations on an image space, for example the same image space, for example by solid lines for active and passive movement as an overlay at display locations on the display of the trajectory of the part of the anatomy.

As a mapping of the trajectory of the part of the anatomy is being performed, the patient can also register points of discomfort or restriction (patient incidence points, PIPs) by pressing a second connected sensor. These patient incidence points may be recorded as an association with the two dimensional coordinate data for comparative purposes. A results table may be automatically populated with data from the current, previous and selected mappings for comparative purposes. In addition, features such as the power, speed or acceleration of movement can be recorded, mapped to an image space, for example the same image space, and overlaid on the display of the trajectory of the part of the anatomy.

FIG. 1 shows a sensor 2 and controller 1 forming an apparatus for mapping the trajectory of a part of the anatomy of the human or animal body. The controller 1 comprises a wireless communications antenna 7 coupled to a wireless communications interface 9. The wireless communications interface 9 is coupled to a processor 11. The processor 11 is coupled to a display 15.

The sensor 2 comprises a wireless communications antenna 17 coupled to a wireless communications interface 19. The wireless communications interface 19 is coupled to a processor 21, which in turn is coupled to sensor elements 23. The sensor elements 23 are coupled to a battery 25, although in some embodiments the processor 21 may be coupled to the battery 25. The sensor 2 may also comprise a charging socket (not shown) to charge the battery 25, and a light, for example an LED, to indicate the mode of operation of the sensor 2. The sensor elements 23 may comprise at least one selected from the list of: accelerometers, gyroscope, air pressure sensors and magnetic field sensors. The sensor elements 23 may also comprise a user-operable interface, for example a button or other means for operation by a user such as a patient or clinician/physiotherapist.

Figure 2A:
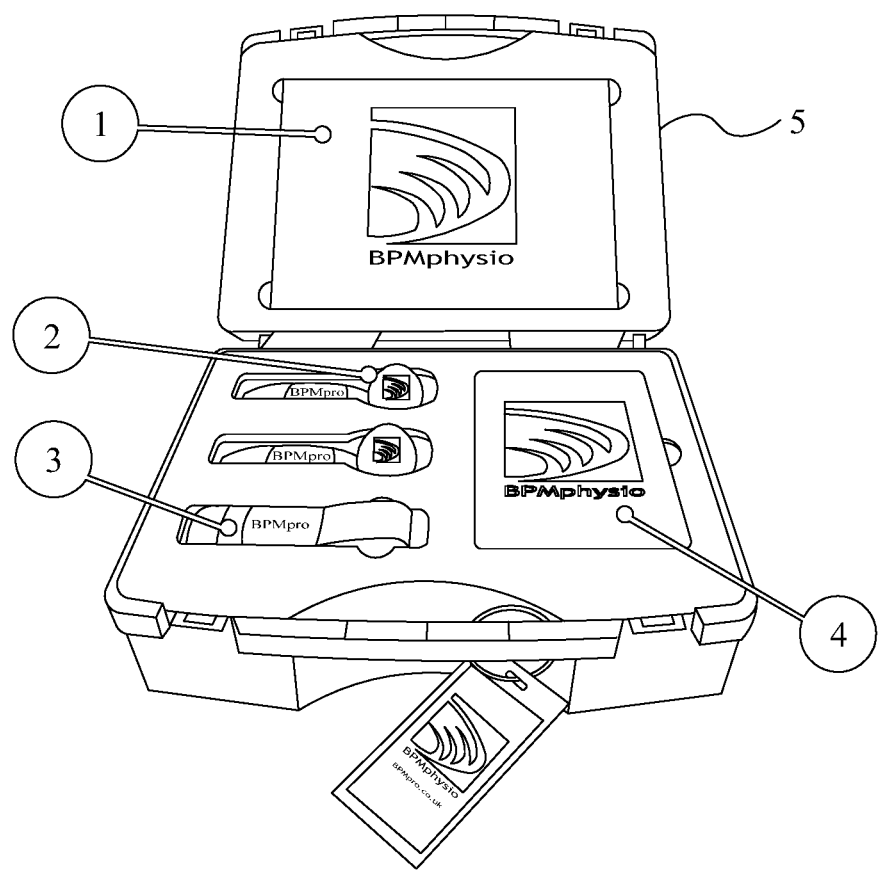
FIG. 2A shows a kit comprising the example apparatus of FIG. 1.

FIG. 2A shows an example kit comprising the apparatus for mapping the trajectory of a part of the anatomy of the human or animal body shown in FIG. 1. FIG. 2A shows a controller 1, two sensors 2, two straps 3 and an accessories compartment 4 optionally comprising accessories such as charging leads, all contained within a case 5. In this example, the controller 1 is a tablet, but it will be understood that the controller 1 could easily by any other computing device and may simply be a processor operable to receive sensor signals, determine angles of rotation from the sensor signals and transform the sensor signals to provide two-dimensional coordinate data. The case 5 is padded, for example with foam, to protect the contents of the case 5 when in transit. Providing the apparatus in a case 5 like this advantageously increases the ease of use and portability of the apparatus.

Figure 2B:
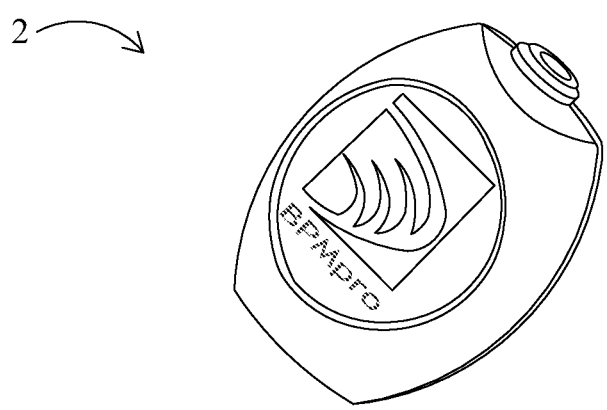
FIG. 2B shows a sensor that forms part of the kit of FIG. 2A.

The sensor 2 of FIG. 2A is shown in more detail in FIG. 2B. The sensor 2 has a unique combination of soft touch, non-marking polymers impregnated with germ-killing silver ion technology in a compact and wearable form factor. The sensor 2 is small, for example less than 50×50×50 mm, for example 48×38×24 mm and lightweight, for example less than 100 g, for example less than 25 g, for example 21 g. The sensor 2 is also shock resistant, for example resistant to at least 4 G, for example at least 10 G, for example at least 32 G. The housing of the sensor may contain Biomaster®, an effective, silver-based anti-microbial technology. Biomaster® is a broad spectrum anti-microbial additive independently tested and proven to reduce bacterial growth by 99.99% within 2 hours, providing durable, lifelong protection against the threat of cross-contamination.

Figure 3:
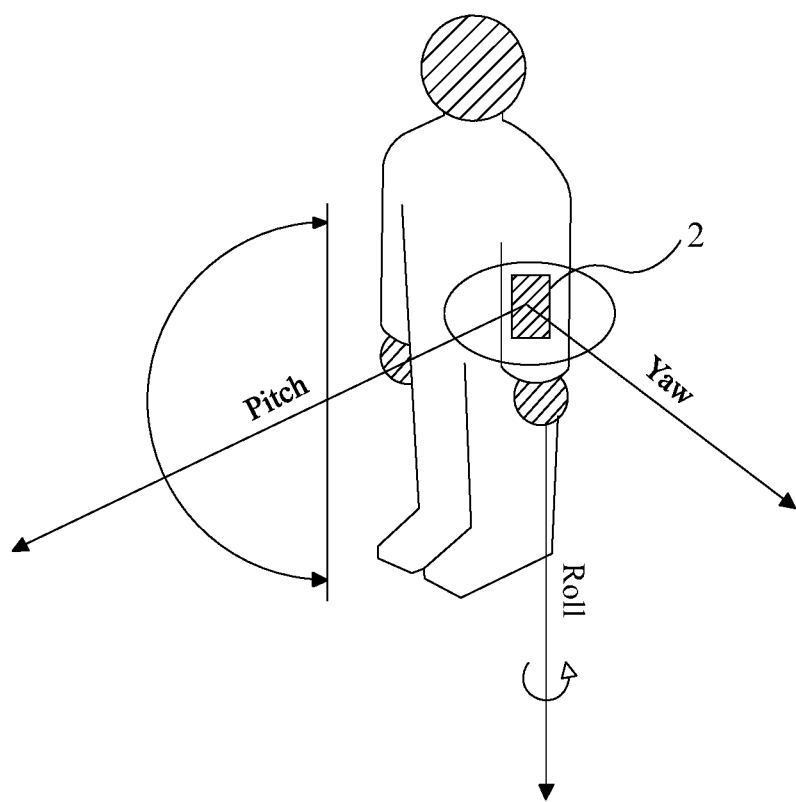
FIG. 3 shows a perspective view of a patient wearing a sensor that forms part of the apparatus of FIG. 1.

The sensor 2 is configured to be attached to a part of the anatomy of the human or animal body, for example as shown in FIG. 3. For example, the sensor 2 may comprise a strap, or means for attaching to a strap, that fastens around a limb of the human or animal body, for example an arm or a leg. Additionally or alternatively, the sensor 1 may comprise means to attach to clothing worn on the part of the anatomy, for example the sensor 1 may comprise a clip or hook and loop material.

The sensor 2 is operable to communicate with the controller 1 to map the trajectory of a part of the anatomy of the human or animal body. In the example shown in FIG. 1, the sensor 2 is configured to communicate wirelessly with the controller 1. The sensor 2 is configured to obtain three dimensional position information indicating the location of the sensor 2, and is operable to transmit this information as first sensor signals to the controller 1. For example, the sensor 2 is configured to obtain the three dimensional position information based on information obtained from sensor elements 23, for example three dimensional position information selected from the list of: orientation relative to the earth's magnetic field, orientation relative to the direction of gravity, and ambient air pressure. The processor 21 of sensor 2 is operable to process information from the sensor elements 23 and via wireless communications interface 19, is operable to produce first sensor signals comprising three dimensional position information indicating the location of the sensor 2.

The controller 1 is configured to receive these first sensor signals comprising the three dimensional position information indicating the location of the sensor 2 from the sensor 2, and the controller 1 is operable to determine at least two angles of rotation of a part of the anatomy of the human or animal body, for example at least two of pitch, yaw and roll as shown in FIG. 3. For example, the controller 1 may be running proprietary software that allows it to perform these functions. The controller 1 is operable to transform the signals received from the sensor 2 to provide two dimensional coordinate data defined in a two dimensional coordinate space such that a first dimension in the two dimensional coordinate space represents a first angle of rotation of the part of the anatomy and a second dimension in the two dimensional coordinate space represents a second angle of rotation of the part of the anatomy. The controller 1 is configured to store the two dimensional data, for example the controller 1 may be coupled to a data storage for storing the two dimensional data. For example, the two dimensional coordinate data may be stored in a tabular format, for example as an XML file. The two dimensional coordinate space may comprise linear coordinate system, for example a rectilinear coordinate system.

In some configurations, the controller 1 is operable to map the first sensor signals to an image space for display of the trajectory of the part of the anatomy, for example on display 15. The image space may comprise instructions for interpretation of data into an image format, for example the image space may be machine readable instructions for display of an image. The image space may comprise data formatted for display in an image, for example a file format, for example a jpg, png or tiff file format. In some configurations, the controller is operable to map the two dimensional coordinate data to an image space for display of the trajectory of the part of the anatomy, for example the controller is operable to map the stored two dimensional coordinate data to an image space. In other configurations, the two dimensional coordinate space may be an image space, such that when the two dimensional coordinate data is transformed to the two dimensional coordinate space it is simultaneously in an image space.

In some configurations, the controller 1 is further operable to obtain a second sensor signal indicative of a third angle of rotation of the part of the anatomy, and is operable to store an association comprising the third angle of rotation and the two dimensional coordinate data indicating the at least two angles of rotation at which the second sensor signal was obtained. For example, the third angle of rotation may comprise the degree of roll of the part of the anatomy. The controller 1 may be configured to map the third angle of rotation of the part of the anatomy to a display location in an image space, for example the same image space, selected based on the stored association. For example, the controller 1 may be configured to display the third angle of rotation of the part of the anatomy as an overlay at the display location on a display of the trajectory of the part of the anatomy.

In some configurations, the controller 1 is further operable to receive a third sensor signal comprising information indicative of an incidence point. The third sensor signal may be obtained from the sensor 2 and operated by the patient, for example from a user operable interface, for example via the use of a button, and may be obtained from the same sensor as the sensor providing the first sensor signals, or from another sensor, for example a sensor operated by a clinician/physiotherapist. The controller 1 may be configured to associate the incidence point with the at least two angles of rotation, for example the two dimensional coordinate data indicating the at least two angles of rotation of the part of the anatomy to record the location of the incidence point. The controller 1 may be configured to store this association between the incidence point and the two dimensional coordinate data. The controller 1 may be configured to map the incidence point to a display location in an image space, for example the same image space, selected based on the stored association. For example, the controller 1 may be configured to display the incidence point as an overlay at the display location on a display of the trajectory of the part of the anatomy.

In some configurations, the controller 1 is further operable to receive a fourth sensor signal comprising information indicative of at least one selected from the list of: speed, acceleration and power of a part of the anatomy of the human or animal body. For example, the sensor signals may be obtained from the sensor 2 and thus obtained from the same sensor providing the first sensor signals, or from another sensor, for example another sensor attached to the patient or a sensor operated by a clinician/physiotherapist. In some configurations, the sensor providing the fourth sensor signals may be the same as the sensor providing the third sensor signals. The controller 1 may be configured to associate the fourth sensor signals with the at least two angles of rotation, for example the two dimensional coordinate data indicating the at least two angles of rotation. The controller 1 may be configured to store this association between the fourth sensor signals, for example at least one selected from the list of: speed, acceleration and power of a part of the anatomy of the human or animal body and the two dimensional coordinate data. The controller 1 may be configured to map the speed, acceleration and/or power to a display location in an image space, for example the same image space, selected based on the stored association. For example, the controller 1 may be configured to display the speed, acceleration and/or power as an overlay at the display location on a display of the trajectory of the part of the anatomy.

In some configurations, the sensor 2 is operable to transmit live data, for example the sensor signals, over a wireless connection, for example a Bluetooth® connection, to the controller 1. For example, the sensor 2 may be operable to transmit the sensor signals to any controller within range, which is typically 10-25 m for a Bluetooth® connection. In some configurations the wireless connection between the controller 1 and sensor 2 is automatic and can detect any sensor 2 within range. In some configurations a plurality of sensors 2, for example two sensors 2, may be connected at the same time enabling real-time direct comparison of data or activities.

In some configurations, the sensor 2 is operable to transmit at a frequency of at least 10 Hz, for example at least 50 Hz, for example at least 100 Hz with latency (delay) for the data (for example the first sensor signals comprising the three dimensional position information) being at least 8 ms, for example at most 40 ms, i.e. about 1/40th of a second. This enables the controller 1 to focus on displaying actual figures in real time, for live feedback, as well as saving the results to a data storage for future reference and comparison.

In some configurations, the sensor 2 is configured to be uniquely identified and paired to the controller 1 using a licence key, for example the sensor 2 is configured to work with a specific controller 1. By using cloud data services such as Dropbox®, patient mapping results can be easily shared across multiple machines in multiple locations, enabling mapping to be carried out at one location and the results reviewed at another location in real time.

The controller 1 may use highly-complex mathematical algorithms to interpret the first sensor signals, and to transform them to map the trajectory of the part of the anatomy to which sensor 2 is attached.

In some configurations, the sensor 2 is operable in a number of different modes of operation. For example, the sensor 2 may be operable in "find" mode, "calibration" mode, "mapping" mode or "sleep" mode. The mode of operation may be displayed somewhere on the sensor, for example the mode of operation may be indicated by a light on the sensor 2, for example a flashing LED. The light may also indicate when the sensor 2 is being charged up or requires charging.

In operation, the sensor 2 and the controller 1 are both switched on and communicating with each other such that signals sent from the sensor 2 are received by the controller 1. The sensor 2 and controller 1 may be communicating in a "mapping" mode where they are operated such that three dimensional position information indicating the location of the sensor 2 is transmitted to the controller 1.

The sensor 2 is worn by a patient on a part of their anatomy, for example a limb, for example their arm. Once the patient and/or clinician/physiotherapist is ready, the patient and/or clinician/physiotherapist can start a mapping, for example by operating the controller 1 or by pressing a button on the sensor 2. Once the mapping begins, the patient moves their part of the anatomy across its range of motion. For example, if the patient is standing upright, the patient may move their arm from right to left and up and down, for example in an arc motion. The mapping may end for example when the patient has reached the limit of their range of motion, after a selected time has elapsed, or when a button, for example a button on sensor 2 or on another sensor operated by a patient and/or a clinician/physiotherapist, is pressed.

At the beginning of the mapping, the sensor elements 23 of the sensor 2 will provide three dimensional position information indicating the location of the sensor 2. For example, the sensor elements 23 may obtain information comprising at least one of: orientation relative to gravity, orientation relative to the earth's magnetic field and air pressure. The processor 21 of sensor 2 processes this information and transmits it to the controller 1 via the wireless communications interface 19 as first sensor signals. The wireless communications interface 9 of the controller 1 receives the first sensor signals, and the controller 1, and specifically the processor of controller 1, transforms the first sensor signals to provide two dimensional coordinate data defined in a two dimensional coordinate space, wherein a first dimension in the two dimensional coordinate space represents a first angle of rotation of the part of the anatomy, and a second dimension in the two dimensional coordinate space represents a second angle of rotation of the part of the anatomy.

As the patient moves their part of their anatomy, the sensor elements 23 detect these movements, for example changes in orientation relative to gravity, changes in orientation relative to the earth's magnetic field and/or changes in air pressure, and the processor 21 of sensor 2 processes this three dimensional position information and sends it as first sensor signals via the wireless communications interface 19 for receipt by the wireless communications interface 9 of the controller 1. In some configurations, the sensor 2 continually outputs first sensor signals to the controller 1, for example regardless of whether the three dimensional position information has changed or not. In other configurations, the sensor 2 only outputs first sensor signals when a change in the three dimensional position information has occurred.

The controller 1 transforms the first sensor signals to provide two dimensional coordinate data defined in a two dimensional coordinate space, wherein a first dimension in the two dimensional coordinate space represents a first angle of rotation of the part of the anatomy, and a second dimension in the two dimensional coordinate space represents a second angle of rotation of the part of the anatomy. The controller 1 then stores the two dimensional coordinate data, for example on an optional data storage coupled to the controller 1 or in some form of data storage comprised in controller 1. In some configurations, the two dimensional coordinate space is a linear two dimensional coordinate space, for example a rectilinear coordinate system.

In configurations where the controller 1 is operable to map the first sensor signals to an image space, the controller 1 maps the first sensor signals to an image space for display of the trajectory of the part of the anatomy. The controller 1 may map the sensor signals to the image space in real time, or near real-time (for example with a delay less than 5 seconds, for example less than 2 seconds, for example less than 1 second from when the movement occurred or from when the signals are received by the controller 1). For example, in some configurations, when the controller 1 transforms the first sensor signals to provide two dimensional coordinate data, the controller 1 also maps the first sensor signals to an image space for display of the part of the anatomy, for example on display 15. For example, the two dimensional coordinate space may also be an image space. In some configurations, the controller 1 maps the two dimensional coordinate data to an image space for display of the part of the anatomy, for example on display 15. For example, in some configurations the controller 1 maps stored two dimensional coordinate data to an image space. In other configurations, the controller 1 maps the two dimensional coordinate data to an image space in real time and simultaneously stores the two dimensional coordinate data. The image space may be in the form of a plot, as shown in FIG. 4.

Figure 4:
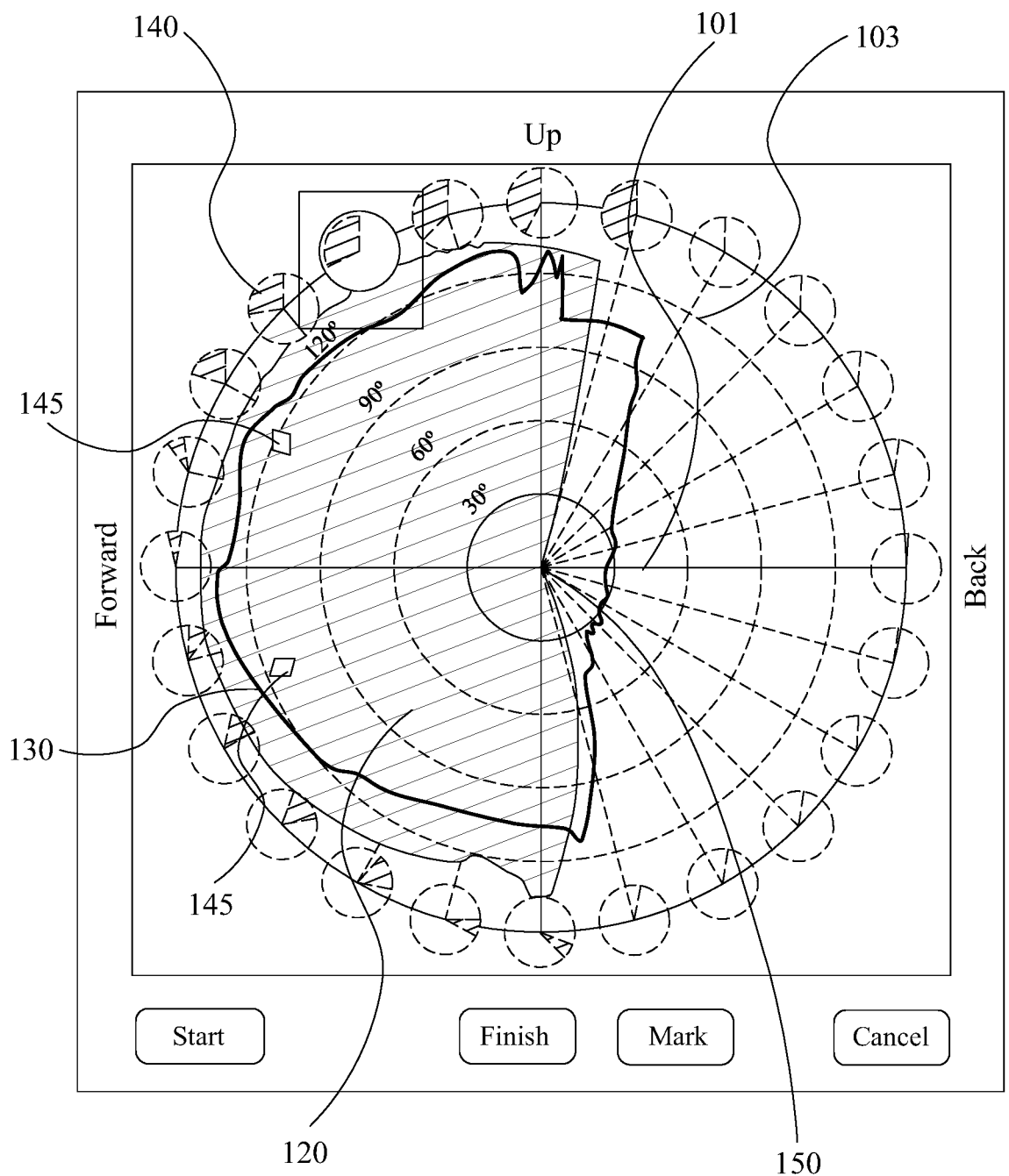
FIG. 4 shows an example plot of the range of motion of a patient's arm using the apparatus of FIG. 1.

The plot shown in FIG. 4 represents an example mapping of the trajectory of an arm to an image space displayed on display 15 of controller 1. The mapping to an image space is in the form of a plot. The plot has two dimensions—one dimension 101 represents one angle of rotation (for example pitch) of the arm, and the other dimension 103 represents another angle of rotation (for example yaw) of the arm. The plot is stereographic in nature, that is the three dimensional position information is displayed on a two dimensional plot, and is conformal in that the angles are preserved. In the plot shown in FIG. 4, the dimension 101 representing pitch is Cartesian, with the relative orientations of the patient's arm with respect to another part of the body, in this case the patient's torso, indicated on the axes. The dimension 103 representing the yaw of the patient's arm is polar in nature; that is the angle of yaw increases with increasing distance from the centre or origin of the plot.

In FIG. 4 the two dimensions are configured to line up so that 0 degrees of pitch and 0 degrees of yaw intersect at the centre or origin 150 of the plot. For example, with the arm horizontal, out to the side, the plot will be at the origin of the plot. As the arm moves forward and (vertically) up, and then (horizontally) to the side, the display reflects that movement. The complete plot (shaded area 120) shows a characteristic "D" profile. By displaying the three dimensional position information on a two dimensional plot in this way, a clinician/physiotherapist can easily determine where the patient has a limited range of motion, or where their range of motion has changed.

The plot displayed in FIG. 4 is preferably taken and displayed in real time, although of course because the transformed signals are stored as two dimensional coordinate data they can be used at a later date and/or compared with each other. FIG. 4 shows the results of a previous mapping shown as an outline 130 overlaid on the plot of the current mapping. In this way, the mapped trajectory of at least one previous mapping can be mapped to an image space, wherein the two dimensional coordinate space and/or image space is the same as for at least one other mapping, and the mapped trajectory of at least one previous mapping can be overlaid on a display of the trajectory of the part of the anatomy from at least one other mapping, for example from stored two dimensional coordinate data.

In some configurations, comparative and differential analysis is used to highlight how different parts of the anatomy of the patient's body, or how different patients are performing at the same time. For example the performance of the left arm can be compared to the right arm, or active use (where the patient is moving their body unaided) compared against passive use (where the clinician/physiotherapist is moving the arm). Patient data may be stored locally, for example on optional data storage coupled to the controller 1, enabling treatment and performance trends to be analysed and compared during and after live mapping. In some configurations the mapped trajectory is compared to "standard" data, for example a "standard" range of motion. The "standard" range figures may be based, for example, on an average 40-year-old man. If the standard maximum range for the movement is exceeded, the controller 1 may be configured to display a warning "out" on display 15, and the mapping restarted. This is to protect the patient from hyperextension and from the mapping being performed incorrectly. An alternative "advanced" range may be used for other patients, for example for use with elite athletes who will likely have an increased range of motion.

In some configurations, where the controller 1 is operable to obtain a second sensor signal indicative of a third angle of rotation of the part of the anatomy, the controller 1 may be configured to map the third angle of rotation of the part of the anatomy to a display location in an image space selected based on the stored association, as shown by the dotted circles 140 in FIG. 4. In FIG. 4, the dotted circles 140 are overlaid on the outer edge of the plot and indicate a third angle of rotation of the arm at that display location, in this case the roll. The shaded area in the overlaid plots 140 indicate the range of motion for that angle of rotation for that particular combination of the other two angles of rotation at that display location.

In configurations where the controller 1 is operable to obtain a third sensor signal comprising information indicative of an incidence point, the controller 1, following receipt of a third sensor signal, stores an association between the incidence point and the two dimensional coordinate data indicating the at least two angles of rotation of the part of the anatomy to record the location of the incidence point. The incidence point may be mapped to a display location in an image space selected based on the stored association, for example so that the incidence point is displayed as an overlay at the display location on a display of the trajectory of the part of the anatomy. For example, using a second sensor the clinician/physiotherapist and/or patient can mark Patient Incidence Points (PIPs) during the mapping to flag any issues arising such as pain or discomfort. PIPs can be marked using, for example a user-operable interface, for example a button or by squeezing the sensor, and this may be confirmed by an audible click. The controller 1 is configured to map the PIPs to the image space such that they appear as an overlay on the plot, for example as an overlay on the mapped trajectory of the part of the anatomy, for example as diamonds 145 overlaid on the plot of the trajectory as shown in FIG. 4. In some configurations, an unlimited number of PIPs can be marked and recorded.

In configurations where the controller 1 is further operable to receive a fourth sensor signal comprising information indicative of at least one of: speed, acceleration or power of a part of the anatomy of the human or animal body. The fourth sensor signals may be obtained from the sensor 2 and thus obtained from the same sensor providing the first sensor signals, or from another sensor, for example a sensor attached to the patient or a sensor operated by a clinician/physiotherapist. For example, the sensor 2 may be used to map the trajectory of a cricketer's arm as he throws a cricket ball. The sensor 2 may be configured to obtain information indicative of the acceleration of the cricketer's arm as it moves. The controller 1 may be configured to associate the fourth sensor signals with the at least two angles of rotation, for example the two dimensional coordinate data indicating the at least two angles of rotation. The controller 1 may be configured to store this association between the fourth sensor signals, for example at least one selected from the list of: speed, acceleration and power of a part of the anatomy of the human or animal body and the two dimensional coordinate data. The controller 1 may be configured to map this information to an image space, for example so that the information is displayed as an overlay at the display location on a display of the trajectory of the part of the anatomy. For example, the speed may be indicated by a change in colour of the mapping of the trajectory of the part of the anatomy in the image space.

In some configurations, the controller 1 is able to support a plurality of sensors 2, for example two sensors 2, for example allowing measurements of left and right limbs simultaneously. When two sensors 2 are communicating with the controller 1, the one on the left can be associated with the left-hand side of the body and the right-hand sensor can be associated with the right-hand side of the body. The active sensor 2 may be highlighted as the appropriate mapping is selected. If the sensors 2 are placed on the wrong sides of the body, they can be swapped over, for example by operation of the controller 1.

The sensor 2 can initiate a mapping without the need to return to the controller 1. For example, if the sensor 2 has a user-operable interface, for example a button, and a mapping is not running, one long press on the button starts the mapping and if the mapping is running, one long press stops the mapping and the mapped trajectory is stored as two dimensional coordinate data.

Figure 5:
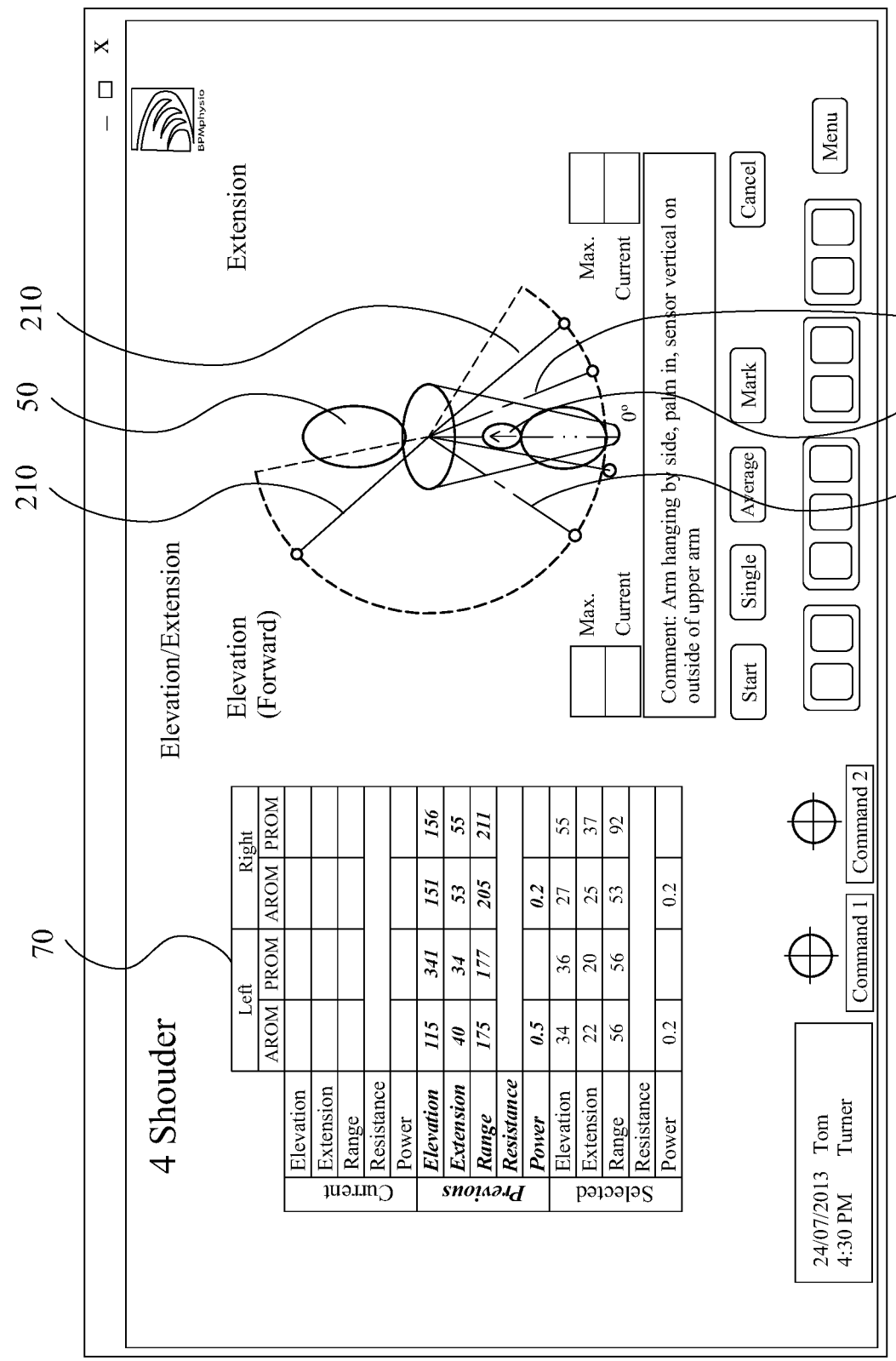
FIG. 5 shows another display of the information obtained using the apparatus of FIG. 1.

The details of any specific data point—for example the three dimensional position information, the determined angles of rotation of the part of the anatomy, or the transformed two dimensional coordinate data—can be displayed in a results table 70 (as shown in FIG. 5), for example by clicking on a display location on the image space. The tabular information 70 may show details of the current, first and a selected previous mapping for comparative purposes.

At least one of the three dimensional position information, the determined angles of rotation of the part of the anatomy, the transformed two dimensional coordinate data, the incidence points and the speed, acceleration and power may also be displayed with respect to an avatar 50. For example, in some configurations, the two dimensional coordinate data is transformed to three dimensional coordinate data defined in a three dimensional coordinate space, and the sensor signals and/or the transformed three dimensional coordinate data mapped to an image space, so that a three dimensional representation of an avatar 50 may be displayed, for example displaying the avatar 50 moving its part of the anatomy, and thus displaying the trajectory of the part of the anatomy on the avatar 50. For example the trajectory of the part of the anatomy may be displayed in real time with the movements of the sensor 2.

In other configurations, the first sensor signals may be transformed to two dimensional coordinate data defined in a two dimensional coordinate space wherein the two dimensions together only represent one angle of rotation of the part of the anatomy. The sensor signals and/or the transformed two dimensional coordinate data may be displayed on an avatar 50, for example as shown in FIG. 5. The image of the avatar 50 in FIG. 5 shows a patient's arm moving, in this example, as they map the trajectory of their arm and hence determine the range of their shoulder abduction (thus only indicating one angle of rotation of the part of the anatomy). The patient's maximum ranges for both passive and active movement are indicated by the lines 205 (active) and lines 210 (passive). In this example, the patient is compared to the vertical position, defined as being perpendicular to the Earth's surface.

In some configurations, sensor signals comprising three dimensional position information indicating the location of the sensor 2 are transformed by the controller 1 to provide three dimensional coordinate data defined in a three dimensional space, wherein one plane indicates a first angle of rotation and a second plane indicates a second angle of rotation. The three dimensional coordinate data may comprise two dimensional coordinate data indicating the at least two angles of rotation of the part of the anatomy.

The sensor signals and/or the transformed three dimensional coordinate data, may be mapped to an image space for display of the trajectory of the part of the anatomy. For example a three dimensional representation of an avatar 50 may be displayed, for example displaying the avatar 50 moving its part of the anatomy, and thus displaying the trajectory of the part of the anatomy. For example the trajectory of the part of the anatomy may be displayed in real time with the movements of the sensor 2. In other configurations, the image space may only show one plane of the three dimensional space, thus only indicating one angle of rotation of the part of the anatomy.

Similarly, in configurations where the controller 1 is operable to receive second, third and/or fourth sensor signals, these may also be displayed with respect to an avatar 50 in a similar way to that described for the first sensor signals described above.

In some configurations, the controller 1 allows the outcome of each mapping to be displayed individually. Alternatively, the outcomes of an unlimited number of mappings can be averaged. The averaged data may then be displayed in a table 70 and/or on an avatar 50. In some configurations PIPs are not averaged as they are deemed to be absolute, the last recorded PIPs, therefore, are those shown on the avatar 50.

The controller 1 may be configured to automatically print to a printer. The screen may print out as it appears on the display 15 and it is important to ensure that the page orientation of the printer is set up appropriately. The printout contains only limited patient information in line with data protection guidelines. A printer driver for a recommended printer is preloaded onto the controller 1.

The controller 1 may be configure to provide "Print" and "Plot" functions so that the patient can leave with a printout of the results of their mapping and a graph of their progress. The plot function also provides clear information in relation to the need for evidence based outcomes. The avatar 50 acts as an aide-memoire of the exercise being performed and the progress chart provides encouragement to the patient to continue with their rehabilitation as they can clearly see and understand the impact of their treatment without having to understand medical terminology. The printout may either comprise the avatar 50 image or historical mapping data.

Patient details such as age, height and weight may be recorded for future use and stored on a data storage coupled to the controller 1 for data protection reasons. This data may encrypted, for example so that it is usable only by the controller 1. Each record may be assigned a universally unique identification reference. A search function may enable the clinician/physiotherapist easily to find an existing record. The subject data may be stored against the patient's details to enable treatment and performance trends to be analysed and compared during and after live mapping.

In some configurations, the patient's history can also be reviewed to see what mappings have been done in the past and a specific set of mappings recalled for analysis during the next live mapping. This enables the current mapping to be compared not only with the first mapping, but also against a set of selected mappings. Data may be saved as in XML format for each patient.

In some configurations, in order for the controller 1 and sensor 2 to communicate with each other, the controller 1 needs to "find" the sensor 2. In order to do this, the sensor 2 and controller 1 are configured to run in "find" mode so that they begin to communicate with each (for example, the sensor 2 and controller 1 are "paired").

In some configurations the controller 1 and the sensor 2 need to be calibrated. This may be done using a "calibration" mode. Once the sensor 2 and the controller 1 are communicating with each other, the sensor 2 can be automatically calibrated by the controller 1 to begin calibration. To improve the calibration procedure, the sensor 2 may be rolled between the palms of a user's hands so that the sensor elements 23 in the sensor 2 experience a wide range of motion. Preferably the sensor 2 is moved in all directions as much as possible.

In some configurations, the controller 1 and/or sensor 2 may operate in "sleep" mode, for example if neither device has been used for a selected period of time, for example at least five minutes, for example at least ten minutes. In "sleep" mode the controller 1 and/or sensor 2 may be quickly activated and switched into "calibration" mode but whilst consuming less power than in "calibration" mode.

An example sensor 2 used in the apparatus and methods disclosed herein has been validated in clinical trials and found to be on a par with OMCS (Optical Motion Capture Systems). These trials compared a single sensor 2 placed at the centre of mass (CoM), lumbar L4, and four Qualisys® cameras. Acceleration, velocity and relative position were compared. The table below shows the results of sensor 2 indicated as BPMpro™ compared based on a single axis result:

|  |  | Acceleration $(MS^{-2})$ | | Velocity $(MS^{-1})$ | | Relative Position (cm) | |
|---|---|---|---|---|---|---|---|
|  |  | BPMpro | OMCS | BPMpro | OMCS | BPMpro | OMCS |
| Subject | 1 | 2.16 ± 0.30 | 2.36 ± 0.26 | 0.40 ± 0.06 | 0.44 ± 0.06 | 4.11 ± 0.40 | 4.22 ± 0.44 |
|  | 2 | 2.65 ± 0.26 | 2.70 ± 0.20 | 0.57 ± 0.05 | 0.57 ± 0.04 | 5.08 ± 0.29 | 4.99 ± 0.40 |
|  | 3 | 1.75 ± 0.17 | 1.92 ± 0.18 | 0.36 ± 0.01 | 0.36 ± 0.01 | 3.34 ± 0.27 | 3.34 ± 0.07 |
|  | 4 | 1.58 ± 0.09 | 1.83 ± 0.10 | 0.31 ± 0.05 | 0.35 ± 0.04 | 3.24 ± 0.38 | 3.33 ± 0.36 |
|  | 5 | 2.38 ± 0.08 | 2.64 ± 0.09 | 0.45 ± 0.01 | 0.47 ± 0.05 | 4.42 ± 0.13 | 4.43 ± 0.48 |

Source: Dr. Patrick Esser, Human Performance Laboratory, Movement Science Group, Oxford Brookes University The BPMpro™ sensor 2 was also interrogated using LabVIEW® 2010 and compared against multi-sensor systems such as Pi-Node®, Xsens® and OPAL®. On the basis that a single BPMpro™ sensor 2 was being compared to multi-camera and multi-sensor systems, the results proved to be not only very useable in a real world environment, but they also demonstrate the cost effectiveness of the methods and apparatus of the present disclosure.

It is suggested that any feature of any one of the examples disclosed herein may be combined with any selected features of any of the other examples described herein. For example, features of methods may be implemented in suitably configured hardware, and the configuration of the specific hardware described herein may be employed in methods implemented using other hardware. In the context of the present disclosure, it will be appreciated that other examples and variations of the apparatus and methods described herein may be provided within the scope of the appended claims.

The processor 11 of the controller 1, and/or the processor 21 of the sensor 2 described herein may comprise a general purpose processor, which may be configured to perform a method according to any one of those described herein. In some examples the controller 1 and/or the sensor 2 and/or the processor 11 and/or the processor 21 may comprise digital logic, such as field programmable gate arrays, FPGA, application specific integrated circuits, ASIC, a digital signal processor, DSP, or any other appropriate hardware.

Where configuration of a processor, or other programmable component, is described this may be achieved by procedural or object oriented programming, or by the use of scripting which incorporates a mixture of both procedural and object oriented approaches. In some cases FGPAs or ASICs may be used to provide these configurations.

The data stores described herein may be provided by volatile or involatile memory storage such as RAM, EEPROM, FLASH memory, or any other form of computer readable media.

What is claimed is:

1. A method for mapping a trajectory of parts of the anatomy of a human or animal body, the method comprising:
    receiving first sensor signals from a first sensor configured for attachment to a first part of the anatomy of the human or animal body, wherein the first sensor signals comprise three dimensional position information indicating a location of the sensor;
    receiving second sensor signals from a second sensor configured for attachment to a second part of the anatomy of the human or animal body, wherein the second sensor signals comprise three dimensional position information indicating a location of the second sensor;
    determining from each of the first and second sensor signals at least two angles of rotation of the first and second parts of the anatomy to which each respective sensor is configured for attachment to perform a comparative analysis to determine how the first and second parts of the anatomy of the human or animal body move at the same time; and
    receiving a third sensor signal comprising information indicative of an incidence point; and
    storing an association between the incidence point and at least two angles of rotation to record a location of the incidence point.

2. The method of claim 1 further transforming the first and second sensor signals to provide two dimensional coordinate data defined in a two dimensional coordinate space, wherein a first dimension in the two dimensional coordinate space represents a first angle of rotation of the part of the anatomy and a second dimension in the two dimensional coordinate space represents a second angle of rotation of the part of the anatomy; and storing the two dimensional coordinate data.

3. The method of claim 2 wherein transforming the signals comprises mapping the signals to an image space for display of the trajectory of the part of the anatomy.

4. The method of claim 3 comprising obtaining a fourth sensor signal indicative of a third angle of rotation of a part of the anatomy and mapping the third angle of rotation to a display location in an image space.

5. The method of claim 4 further comprising displaying the third angle of rotation of the part of the anatomy as an overlay at the display location on a display of the trajectory of the part of the anatomy.

6. The method of claim 2 wherein transforming the first and second sensor signals to a two dimensional coordinate space comprises at least one of (i) transforming the first and second sensor signals to a linear two dimensional coordinate space, (ii) a conformal transformation and (iii) applying a stereographic projection.

7. The method of claim 2 comprising transforming the first and second sensor signals such that pitch and yaw are provided on the two dimensional coordinate space.

8. The method of claim 1 comprising comparing the determined at least two angles of rotation with a data set.

9. The method of claim 1 further comprising mapping the incidence point to a display location in an image space selected based on the stored association and displaying the incidence point as an overlay at the display location on a display of the trajectory of the part of the anatomy.

10. The method of claim 1, further comprising:
    receiving fifth sensor signals comprising information indicative of at least one of speed, acceleration or power of a part of the anatomy of the human or animal body; and
    associating (i) the fifth sensor signals with (ii) the at least two angles of rotation of the part of the anatomy to record at least one of the speed, acceleration or power as a function of the at least two angles of rotation of the part of the anatomy.

11. The method of claim 10 further comprising mapping at least one of the speed, acceleration or power to an image space to display the function as an overlay on a display of the trajectory of the part of the anatomy.

12. The method of claim 1 further comprising mapping the first and second sensor signals to an image space, and mapping stored two dimensional coordinate data to the image space, for display of the trajectory of the part of the anatomy as an overlay on a display of the trajectory of the part of the anatomy mapped to the image space from the stored two dimensional coordinate data.

13. The method of claim 1, comprising:
    determining from the first sensor signals at least two angles of rotation of the part of the anatomy of the human or animal body to which the first sensor is configured for attachment to with respect to a centre of rotation of another part of the body, wherein the angles of rotation are selected from pitch, yaw and roll;
    determining from the second sensor signals at least two angles of rotation of the part of the anatomy of the human or animal body to which the second sensor is configured for attachment to with respect to a centre of rotation of another part of the body, wherein the angles of rotation are selected from pitch, yaw and roll;
    transforming the first and second sensor signals to provide three dimensional coordinate data defined in a three dimensional space, wherein one plane indicates a first angle of rotation and a second plane indicates a second angle of rotation, and wherein the three dimensional coordinate data comprises two dimensional coordinate data indicating the at least two angles of rotation of the part of the anatomy; and
    storing the three dimensional coordinate data.

14. An apparatus for mapping a trajectory of parts of the anatomy of a human or animal body, the apparatus comprising:
    a first sensor for attaching to a first part of the anatomy of the human or animal body; and a second sensor for attaching to a second part of the anatomy of the human or animal body; a third sensor for indicating an incidence point;
    a processor for receiving first sensor signals from the first sensor, second sensor signals from the second sensor, and third sensor signals comprising information indicative of the incidence point from the third sensor, wherein the first and second sensor signals comprise three dimensional position information indicating a location of the respective sensors;

wherein the processor is configured to determine at least two angles of rotation of the each of the first and second parts of the anatomy of the human or animal body to which each respective sensor is configured for attachment to in order to perform a comparative analysis to determine how the different first and second parts of the anatomy of the patient's body move at the same time; and wherein the processor is configured to store an association between the incidence point and at least two angles of rotation to record a location of the incidence point.

15. The apparatus of claim 14, wherein the processor is configured to transform the first sensor signals received from the first sensor and the second sensor signals received from the second sensor to provide two dimensional coordinate data defined in a two dimensional coordinate space such that a first dimension in the two dimensional coordinate space represents a first angle of rotation of the part of the anatomy, and a second dimension in the two dimensional coordinate space represents a second angle of rotation of the part of the anatomy, and store the two dimensional coordinate data.

16. The apparatus of claim 15 wherein the processor is configured to map the first and second sensor signals to an image space for display of the trajectory of the part of the anatomy.

17. The apparatus of any of claim 14 wherein the processor is further configured to obtain a fourth sensor signal indicative of a third angle of rotation of a part of the anatomy, and wherein the processor is further configured to map the third angle of rotation to a display location in an image space and display the third angle of rotation of the part of the anatomy as an overlay at the display location on a display of the trajectory of the part of the anatomy.

18. The apparatus of claim 14 wherein the processor is configured to at least one of:

(i) transform the received first and second sensor signals to a linear two dimensional coordinate space, (ii) transform the received first and second sensor signals with a conformal transformation and (iii) transform the received signals by applying a stereographic projection.

19. The apparatus of claim 14 wherein the processor is configured to map the third sensor signals to an image space for display of the incidence point at a display location selected based on the stored association, and to display the incidence point as an overlay on a display of the trajectory of the part of the anatomy.

20. The apparatus of claim 14 wherein the processor is configured to determine from the first sensor signals at least two angles of rotation of the part of the anatomy of the human or animal body to which the first sensor is configured for attachment to with respect to a centre of rotation of the body, wherein the angles of rotation are selected from pitch, yaw and roll; and wherein the processor is configured to determine from the second sensor signals at least two angles of rotation of the part of the anatomy of the human or animal body to which the second sensor is configured for attachment to with respect to a centre of rotation of the body, wherein the angles of rotation are selected from pitch, yaw and roll; and the processor is configured to transform the first sensor signals and the second sensor signals to provide three dimensional coordinate data defined in a three dimensional coordinate space, wherein one plane indicates a first angle of rotation of the part of the anatomy and the second plane indicates a second angle of rotation of the part of the anatomy, and wherein the three dimensional coordinate data comprises two dimensional coordinate data indicating the at least two angles of rotation, and the processor is configured to store the three dimensional coordinate data.

\* \* \* \* \*